United States Patent [19]

Garlen

[11] 4,381,920
[45] May 3, 1983

[54] METHOD AND COMPOSITION FOR DYEING HUMAN HAIR

[75] Inventor: David Garlen, Roselle Park, N.J.

[73] Assignee: Michael-David Laboratories, Roselle Park, N.J.

[21] Appl. No.: 294,569

[22] Filed: Aug. 20, 1981

Related U.S. Application Data

[63] Continuation-in-part of Ser. No. 63,443, Aug. 3, 1979, abandoned, which is a continuation-in-part of Ser. No. 929,670, Jul. 31, 1978, abandoned, which is a continuation-in-part of Ser. No. 741,513, Nov. 15, 1976, abandoned.

[51] Int. Cl.³ .............................................. D06P 3/52
[52] U.S. Cl. ............................................ 8/406; 8/407
[58] Field of Search ............................ 8/405, 406, 407

[56] References Cited

U.S. PATENT DOCUMENTS

| | | | |
|---|---|---|---|
| 2,769,748 | 11/1956 | Eckardt et al. | 8/406 |
| 3,811,830 | 5/1974 | De Marco | 8/405 |
| 3,911,105 | 10/1975 | Papantoniou et al. | 424/70 X |
| 3,920,384 | 11/1975 | Feinland et al. | 8/406 |

FOREIGN PATENT DOCUMENTS

| | | | |
|---|---|---|---|
| 344529 | 11/1921 | Fed. Rep. of Germany | 8/406 |
| 653053 | 5/1951 | United Kingdom | 8/406 |
| 988914 | 4/1965 | United Kingdom | 8/406 |
| 1076127 | 7/1967 | United Kingdom | 8/406 |

OTHER PUBLICATIONS

Poucher, Perfumes, Cosmetics & Soaps, vol. I, Chapman & Hall Ltd., England, 1959, p. 402.

*Primary Examiner*—Dale R. Ore
*Attorney, Agent, or Firm*—Mason, Kolehmainen, Rathburn & Wyss

[57] ABSTRACT

Keratinous materials, such as human hair, can be colored stepwise in gradual increments at ambient temperatures with formulations of selected oxidation hair dye intermediates with an oxidizing agent at pH in the range from 7.0 to 8.3 in a white relatively odorless cream vehicle. Sequential application of the cream vehicle formulations, rinsed after a period of time, followed by application of an oxidizing agent, do not stain or color the skin, can be easily applied to the hair and color the hair slowly in steps over a period of weeks, resulting in a gradual color change to any desired shade from light brown to black.

1 Claim, No Drawings

METHOD AND COMPOSITION FOR DYEING HUMAN HAIR

CROSS-REFERENCE TO RELATED APPLICATIONS

This application is a continuation-in-part of Ser. No. 063,443, filed Aug. 3, 1979, (now abandoned) which is a continuation-in-part of Ser. No. 929,670, filed July 31, 1978, (now abandoned), which is a continuation-in-part of Ser. No. 741,513, filed Nov. 15, 1976 (now abandoned).

This invention relates to a colorless hair coloring preparation. More particularly this invention relates to a white cream emulsion hair coloring preparation particularly adapted and designed for use on men's hair and to a unique method of application of said hair color emulsion to gradually dye the hair.

BACKGROUND OF THE INVENTION

Coloring agents for men's hair are and have been traditionally produced in the form of white emulsions which are rubbed on the hair daily and which, over a period of days and often weeks, produce a darker color on the hair. Generally they are used to darken grey hair, and produce brown or black shades thereon. For customer acceptance, such hair coloring preparations should be in the form of essentially clear liquids or white creams or lotions which do not stain the skin, particularly the hands, and should not contribute any coloring effect to the hair at the time when they are applied thereto. Such hair coloring preparations are applied to the hair in the same way that ordinary hair dressings are applied which do not have hair coloring properties, that is by hand application with combing and brushing to arrange the hair. The concept behind such hair coloring preparations is that they are rubbed on in the same manner as hair dressings and they make no noticeable effect on the hair until several days after application. After a series of applications they bring about the desired slow color change of the hair over a period of days or weeks.

To date the hair coloring preparations of this type have all contained lead salts, genreally lead acetate. These lead salts, when applied to the hair in a colorless formulation, gradually decompose and oxidize in the air to lead dioxide and/or to lead sulfide, both of which are dark pigments which color the hair to one of the darker shades. Lead salts are, however, toxic and hair dressings and coloring formulations which contain lead salts have created serious questions as to their safety. Furthermore such preparations result in unnatural looking hair, tend to rub off on clothing and bedlinens, and have a metallic sheen. Consequently it has long been the desire of the hair coloring industry to obtain colorless hair formulations which do not contain lead compounds, which can be hand-applied to the hair to convert it to a darker hue gradually over a period of time.

In conventional hair color preparations oxidation dyes are usually adjusted to a pH of 9.0 to 10.0 with ammonia. Those preparations on the market with a pH as low as 7.5 to 8.0 require pre-bleaching of the hair to obtain the desired shades. These prior products, while they give natural looking and permanent hair coloring resultsm, are dark in color, require considerable technique in application, have a strong ammoniacal odor, stain the skin, and are generally not favored for home use by men.

OBJECTS OF THE INVENTION

It is an object of this invention to provide lead-free colorless hair preparations which can be easily applied to the hair and which over a number of applications form colored dyes in the interstices of the hair, thus causing dyeing of grey hair to brown or blacker shades. A further object is to provide a white, colorless hair dye emulsion which will not stain the hands or the skin when being applied to the hair, which will not stain fabrics which come in contact with hair treated with it, and which will gradually form a colored dye in the hair, without unpleasant odor.

Another object is to provide a method of coloring the hair gradually by forming dyes within the interstices of the hair in a series of steps.

These and other objects are accomplished in accordance with the following description of the invention.

GENERAL DESCRIPTION OF THE INVENTION

I have discovered that colorless hair formulations can be produced by incorporating certain oxidation dye intermediates at low concentration in an oil-in-water emulsion of relatively low pH containing inert white pigments to form a white cream which is colorless on the skin and yet will form colored dyes in the hair over a period of time after oxidation with a suitable oxidizing agent.

In the formulations which comprise this invention it has been found that combinations of only a small number of oxidation dye intermediates can be used as the dye component. These materials must be effective at low concentration (1.5% by weight or lower) and must be stable in a formulation which is protected from atmospheric oxygen. I have discovered that certain oxidation dye intermediates are suitable in hair coloring preparations of the type discussed. These are combinations of the oxidation dye intermediate p-phenylenediamine, with color modifiers selected from resorcinol, 4-chlororesorcinol, p-aminophenol, and/or 4-chloro-m-phenylenediamine, which combinations have been found to be suitable for the production of dyes in human hair. The amino compounds are colorless in the formulation but upon exposure to oxygen they become oxidized to brown or black dyes which serve to color the hair. The total concentration of these components in the white aqueous emulsion must be kept below 1.5% by weight and their relative proportions must be selected both with regard to effect on the color of the emulsion as well as the final color that develops in the interstices of the hair.

DETAILED DESCRIPTION OF THE INVENTION

In accordance with this invention, hair color preparations are produced which are effective at relatively low alkalinity, that is at pH values below 8.5, preferably at pH 7.9 to 8.3. The preparations contain a combination of an oxidation dye intermediate and one or more color modifiers in emulsion form (oil-in-water with conventional emulsifying agents, preferably nonionic) with a white pigment such as titanium dioxide suspended therein.

The procedure is to apply the colorless hair color formulation to the hair and allow it to remain thereon for 15-30 minutes after which the excess formulation is washed off. In this step the dye intermediate is absorbed into the hair cells and interstices, and is not on the surface. Then the oxidizing agent, preferably in the form of an aqueous gel, is applied and left on the hair for 15 minutes, followed by a second washing. The oxidizing agent, on contact with the hair, reacts with the dye intermediate and modifier therein and forms a dye in the hair cells or insterstices. This procedure can be repeated until the desired shade is attained.

By use of the procedure and preparations of this invention it is possible to achieve good results by use of conventional oxidation dye intermediates in a vehicle consisting of waxes, oils, and emulsifiers in the presence of suitable anti-oxidants, water and preservatives. Such hair coloring formulation is capable of being used, in conjunction with dilute hydrogen peroxide, preferably in gel form, to provide hair coloring in a series of weekly applications. In comparison to lead acetate cream hair color dressing, this product provides more intense and more natural looking color, avoids the metallic sheen prevalent in the lead acetate hair coloring and avoids the odor characteristic of this type of hair coloring.

The formulations of this application are in white cream form in contrast to conventional oxidation hair colors which are traditionally dark in color. The formulations of this application are essentially odorless or lightly perfumed in comparison with conventional hair colors which, due to their high ammonium hydroxide content, have a strong ammoniacal and unpleasant odor. In comparison with conventional hair colors, these formulations accomplish the hair coloring operation at a pH from 7.9 to 8.3, as contrasted with the conventional hair colors where the pH of the product is invariably highly alkaline. Moreover, these formulations do not color or stain the skin and can be applied by hand. Furthermore, such compositions are effective in a single shade suitable for all brown hair colors ranging from light brown to brown-black, in contrast to conventional oxidation colors that require a whole series of formulas, each for a specific hair shade.

The hair color composition in its preferred embodiment comprises an oil-in-water non-ionic emulsion, containing in the oil phase mineral oil in a concentration from 2 to 20%, water in a concentration of 50 to 80%, and suitable emulsifiers and bodying agents, preferably non-ionic, and consisting of fatty alcohols such as cetyl or stearyl alcohol; ethoxylated fatty alcohols, such as ethoxylated cetyl or stearyl alcohol; glycol stearates, such as glyceryl monostearate, propylene glycol monostearate; surface active agents such as sodium lauryl sulfate or soap.

The foregoing ingredients are formed into a soft creamy consistency by usual oil-in-water emulsion technology. In addition suitable preservatives, such as esters of parahydroxybenzoic acid, may be employed. A humectant such as glycerol or sorbitol is desirable to prevent drying out of the cream. Certain oxidation dye intermediates, described below, comprise the dye-forming portion. A suitable antioxidant, such as sodium sulfite, is employed to avoid darkening of the cream in its container, and an opacifier or whitening agent, such as zinc oxide, magnesium oxide, or titanium dioxide, is used to whiten the cream. A suitable fragrance may be added for esthetic purposes.

Selection of the appropriate combination of dye-forming intermediates is important in determining the series of shades of the hair color to be achieved. Suitable combinations of dye-forming intermediates which have been found to be effective in the hair coloring compositions of this specification include the following, the percentages being based on the weight of the complete formulation:

|  | Min. % | Max. % |
|---|---|---|
| I | | |
| p-Phenylenediamine | 0.5 | 1.3 |
| Resorcinol | 0.01 | 0.1 |
| II | | |
| p-Phenylenediamine | 0.5 | 1.3 |
| 4-Chlororesorcinol | 0.01 | 0.1 |
| III | | |
| p-Phenylenediamine | 0.5 | 1.3 |
| Resorcinol | 0.01 | 0.1 |
| p-Aminophenol | 0.01 | 0.1 |
| IV | | |
| p-Phenylenediamine | 0.5 | 1.3 |
| 4-Chlororesorcinol | 0.01 | 0.1 |
| p-Aminophenol | 0.01 | 0.1 |
| V | | |
| p-Phenylenediamine | 0.5 | 1.3 |
| 4-Chlororesorcinol | 0.01 | 0.1 |
| 4-Chloro-m-phenylene-diamine sulfate | 0.01 | 0.1 |
| VI | | |
| p-Phenylenediamine | 0.5 | 1.3 |
| Resorcinol | 0.01 | 0.1 |
| 4-Chloro-m-phenylene-diamine sulfate | 0.01 | 0.1 |

The invention is further disclosed by the following examples which illustrate a typical hair coloring formulation of this invention and its application to human hair. It will be understood by those skilled in the art that various modifications of these examples may be made within the general parameters set forth above. Percentages are given by weight, based on the complete hair color formulation.

EXAMPLE 1

|  | Wt. % |
|---|---|
| A - Oil phase | |
| Mixture of cetearyl alcohol and ceteareth 20 | 2.00 |
| Propylene glycol monostearate | 3.00 |
| Polyethylene glycol 100 monostearate | 1.00 |
| Cetyl alcohol (N.F.) | 2.00 |
| Propyl parpaben (U.S.P.) | 0.05 |
| Stearic acid (T.P.) | 0.50 |
| B - Water phase | |
| Water (deionized) | 77.00 |
| Methyl paraben (U.S.P.) | 0.15 |
| Disodium ethylenediaminetetraacetate | 0.10 |
| Sodium sulfite | 1.00 |
| Propylene glycol | 6.00 |
| C - Dye Phase | |
| p-Aminophenol | 0.05 |
| 4-Chlororesorcinol | 0.05 |
| D - Pigment phase | |
| Titanium dioxide (No. 325) Propylene glycol | 2.00 |
| E - Neutralizer | |
| Diisopropanolamine (10%) | 2.00 |
| Perfume | 0.15 |

Cetearyl alcohol is a mixture of cetyl and stearyl alcohols. Ceteareth 20 is a 20-mole ethylene oxide adduct of cetearyl alcohol.

Manufacturing Procedure

1. In a stainless steel jacketed kettle equipped with agitation, combine ingredients of Phase A and heat to 75° C.
2. In a separate stainless steel jacketed kettle of sufficient size to accommodate entire batch, equipped with variable speed agitation, add deionized water and start heating to 75° C. Add other ingredients of Phase B and heat to 75° C. with agitation until phase is clear with no undissolved solids.
3. Set up nitrogen cylinder and direct flow over surface of Phase B.
4. Add ingredients of Phase C to Phase B with agitation, continue mixing until completely dissolved.
5. Disperse titanium dioxide in propylene glycol (Phase D) and pass through colloid mill. Add Phase D to Phase B+C with good agitation.
6. Add Phase A to Phase BCD with agitation, then cool to 45° C.
7. Add Phase E and Phase F with agitation. The resulting hair color formulation is colorless.
8. Cool hair color formulation to 30° C. and fill into aluminum tubes under nitrogen.
9. Protect formulation from air exposure at all times.

| Activator (Oxidant) | Wt. % |
| --- | --- |
| Phase A | |
| Deionized water | 66.39 |
| Phenacetin | 0.04 |
| Phase B | |
| Hydrogen peroxide (35%) | 8.57 |
| Phase C | |
| Poloxamer 407 | 25.00 |
| Phase D | |
| Phosphoric acid (85%) | q.s. to pH 3.0 |

Manufacturing Procedure

1. In a stainless steel jacketed kettle that has been passivated for peroxide dilution, equipped with agitation, heat water to 80° C., dissolve phenacetin with agitation. Cool to 25° C. Add Phase B.
2. Cool to 5°–10° C. Slowly sprinkle in Phase C. Mix until dissolved.
3. Slowly add Phase D until pH=3.0.
4. Warm batch to 25° C. It will gel as temperature is raised. Fill at about room temperature (20°–30° C.).

Poloxamer 407 is a poloxyethylene-polyoxypropylene block polymer of the general formula $$HO(CH_2CH_2O)_x[CH(CH_3)CH_2O]_y(CH_2CH_2O)_zH$$

wherein x and z are 98 and y is 67.

Application To Hair

The procedure is to apply the colorless hair color formulation to the hair and allow it to remain thereon for 15–30 minutes after which the excess formulation is washed off. In this step the dye intermediate is absorbed into the hair cells and interstices, and is not on the surface. Then the activator gel is applied and left on the hair for 5–15 minutes, followed by a second washing. The activator, on absorption into the hair, reacts with the dye intermediate and forms the dye in the hair cells. This procedure is repeated weekly until the desired shade is attained.

EXAMPLE 2

| | Wt. % |
| --- | --- |
| A - Oil phase | |
| Mixture of cetearyl alcohol and ceteareth 20 | 6.0 |
| Self-emulsifying propylene glycol monostearate (5% potassium stearate) | 4.0 |
| Light mineral oil | 11.0 |
| Propyl paraben (U.S.P.) | 0.05 |
| B - Water phase | |
| Water (deionized) | 73.11 |
| Methyl paraben (U.S.P.) | 0.15 |
| Sodium sulfite | 0.4 |
| p-Phenylenediamine | 0.22 |
| Resorcinol | 0.04 |
| p-Aminophenol | 0.04 |
| Titanium dioxide | 0.25 |
| Glycerol | 4.0 |
| Perfume | 0.15 |

After combination of the oil and water phases at a temperature of 60° to 70° C., the product is cooled to 45°–50° C. and perfume is added. The product is then cooled to room temperature and immediately packed into airtight containers and topped with nitrogen to prevent premature oxidation.

EXAMPLE 3

| | Wt. % |
| --- | --- |
| A - Oil phase | |
| Mixture of cetearyl alcohol and ceteareth 20 | 6.0 |
| Self-emulsifying propylene glycol monostearate (5% potassium stearate) | 4.0 |
| Light mineral oil | 11.0 |
| Propyl paraben (U.S.P.) | 0.05 |
| B - Water phase | |
| Water (deionized) | 73.11 |
| Methyl paraben (U.S.P.) | 0.15 |
| Sodium sulfite | 0.4 |
| p-Phenylenediamine | 0.8 |
| 4-Chlororesorcinol | 0.05 |
| 4-Chloro-m-phenylenediamine sulfate | 0.04 |
| Titanium dioxide | 0.25 |
| Glycerol | 4.0 |
| Perfume | 0.15 |

After combination of the oil and water phases at a temperature of 60° to 70° C., the product is cooled to 45°–50° C. and perfume is added. The product is then cooled to room temperature and immediately packed into airtight containers and topped with nitrogen to prevent premature oxidation.

EXAMPLE 4

| Phase | Ingredient | Percent by Weight |
| --- | --- | --- |
| A | Mixture of cetearyl alcohol and ceteareth 20 | 6.00 |
| A | Self-emulsifying propylene glycol monostearate (5% potassium stearate) | 4.00 |
| A | Carnation oil 65/75 | 11.00 |
| A | Propyl paraben | 0.05 |

-continued

| Phase | Ingredient | Percent by Weight |
|---|---|---|
| B | Deionized water | 73.15 |
| B | Methyl paraben | 0.15 |
| B | Sodium Sulfite | 0.40 |
| C | p-Phenylenediamine | 0.80 |
| C | 4-Chlororesorcinol | 0.05 |
| D | Titanium dioxide (328) | 0.25 |
| D | Glycerin (96%) | 4.00 |
| E | Perfume | 0.15 |
|   | TOTAL | 100.00 |

Procedure:

1. In a stainless steel jacketed kettle equipped with agitation combine ingredients of Phase A and heat to 75° C.

2. In a separate vessel, combine ingredients of Phase B and heat to 80° C.

3. In a third kettle, blend ingredients of Phase C.

4. Place Phase B under a blanket of nitrogen and slowly add Phase C. Maintain heat and continue mixing until dyestuffs are completely dissolved.

5. In another vessel sprinkle titanium dioxide in glycerin, extending slowly until completely dispersed (Phase D).

6. Add Phase D to Phase B.

7. Add the Phase A to the Phase B. Begin cooling.

8. At 45° C. add Perfume.

9. Cool to 30° C. and fill into lined aluminum tubes.

This preparation is a white odorless emulsion which is stable in metal tubes.

SUMMARY OF THE INVENTION

The hair coloring preparation which constitutes this invention comprises the following components:

(a) an oil-in-water emulsion of 5 to 20 parts by weight of oil in 80 to 95 parts of water with conventional emulsifying agents, preferably nonionic;

(b) p-phenylenediamine at a concentration of about 0.5% to about 1.5% of weight of the oil-in-water emulsion;

(c) a white pigment suspended in the emulsion in quantity sufficient to produce a creamy white product, usually about 0.2% to 1% by weight of the total preparation;

(d) an antioxidant in quantity sufficient to prevent premature oxidation of the oxidation dye intermediate, usually about 0.2% to 1% by weight of the total preparation;

(e) and one or more color modifiers selected from 4-chlororesorcinol, 4-chloro-m-phenylenediamine, resorcinol, and p-aminophenol to vary the color produced by oxidation of the dye intermediate of part (b). The modifiers amount to about 10% to 50% the weight of the p-phenylenediamine oxidation dye intermediate.

The hair coloring preparation is adjusted to a pH in the range of 7 to 8.3, preferably with citric acid or triethanolamine depending on initial pH. It is stable when packaged with the exclusion of air. When applied to the hair, the oxidation dye intermediate or the combination of dye intermediate contained in the preparation is absorbed into the hair and sufficient dye intermediates and modifiers are entrapped to survive rinsing. Hydrogen peroxide is applied to oxidize the entrapped intermediates to a permanent color. Each successive weekly application darkens the shade until desired shade is reached.

I claim:

1. A method of dyeing human hair which comprises the steps of:

(1) application to the hair of a hair color formulation comprising:

(a) an oil-in-water emulsion of 5 to 20 parts by weight of oil in 80 to 95 parts by weight of water;

(b) p-phenylenediamine at a concentration of about 0.5% to about 1.5% of the weight of the oil-in-water emulsion;

(c) 4-chlororesorcinol as a dye color modifier, in quantity equal to 10% to 50% of the weight of the p-phenylenediamine;

(d) an inert white pigment suspended in the emulsion at a concentration of about 0.2% to about 1% of the weight of the total formulation; and (e) an antioxidant in quantity sufficient to prevent premature oxidation of the p-phenylenediamine oxidation dye intermediate when packaged out of contact with air;

(f) the total quantity of oxidation dye intermediates being not greater than 1.5% of the total weight of the formulation and (g) the pH of said formulation being between 7.0 and 8.3, (2) allowing said formulation to remain on the hair for 15–30 minutes, (3) rinsing off the excess, and (4) application of an excess of dilute hydrogen peroxide which is allowed to remain on the hair for 5–15 minutes and then rinsed off.

* * * * *